(12) United States Patent
Solomon et al.

(10) Patent No.: US 7,838,031 B2
(45) Date of Patent: Nov. 23, 2010

(54) METHOD OF ADMINISTERING A PARTIAL DOSE USING A SEGMENTED PHARMACEUTICAL TABLET

(76) Inventors: Lawrence Solomon, 7810 Afton Villa Ct., Boca Raton, FL (US) 33433; Allan S. Kaplan, 7011 Mallorca Crescent, Boca Raton, FL (US) 33433

( * ) Notice: Subject to any disclaimer, the term of this patent is extended or adjusted under 35 U.S.C. 154(b) by 885 days.

(21) Appl. No.: 11/441,455

(22) Filed: May 25, 2006

(65) Prior Publication Data
US 2007/0031494 A1 Feb. 8, 2007

Related U.S. Application Data

(63) Continuation-in-part of application No. PCT/US2005/018631, filed on May 23, 2005, and a continuation-in-part of application No. PCT/US2005/018632, filed on May 23, 2005.

(60) Provisional application No. 60/573,042, filed on May 21, 2004, provisional application No. 60/573,134, filed on May 21, 2004.

(51) Int. Cl.
*A61K 9/44* (2006.01)
(52) U.S. Cl. .................... 424/467; 424/465; 424/472
(58) Field of Classification Search .................. 424/467
See application file for complete search history.

(56) References Cited

U.S. PATENT DOCUMENTS

| | | | |
|---|---|---|---|
| 3,128,226 A | 4/1964 | Rubin et al. | |
| 3,336,200 A | 8/1967 | Krause et al. | |
| 3,517,871 A | 6/1970 | Gaffney et al. | |
| 3,696,091 A | 10/1972 | Eberlein et al. | |
| 3,723,614 A * | 3/1973 | Langauer | 424/467 |
| 3,927,194 A | 12/1975 | Geller et al. | |
| 4,139,589 A | 2/1979 | Beringer et al. | |
| 4,215,104 A | 7/1980 | Ullman et al. | |
| 4,258,027 A | 3/1981 | Ullman et al. | |
| 4,353,887 A | 10/1982 | Hess et al. | |
| 4,503,031 A * | 3/1985 | Glassman | 424/467 |
| 4,590,183 A | 5/1986 | Bailey et al. | |
| 4,824,677 A | 4/1989 | Shah et al. | |
| 5,041,430 A | 8/1991 | Addicks et al. | |
| 5,158,728 A | 10/1992 | Sanderson | |
| 5,562,920 A | 10/1996 | Demmer et al. | |
| 5,817,340 A | 10/1998 | Roche et al. | |
| 6,086,919 A | 7/2000 | Bauer et al. | |
| 6,183,778 B1 | 2/2001 | Conte et al. | |
| 6,294,200 B1 | 9/2001 | Conte et al. | |
| 6,309,668 B1 | 10/2001 | Bastin et al. | |
| 6,555,581 B1 | 4/2003 | Franz et al. | |
| 6,827,947 B2 | 12/2004 | Lofroth et al. | |
| 6,919,373 B1 | 7/2005 | Lam et al. | |
| 7,011,849 B2 | 3/2006 | Storm et al. | |
| 2002/0132850 A1 | 9/2002 | Bartholomaus | |
| 2005/0038039 A1 | 2/2005 | Fanara et al. | |
| 2006/0280794 A1 | 12/2006 | Hamaguchi et al. | |

OTHER PUBLICATIONS

H.A. Lieberman and L. Lachman, Pharmaceutical Dosage Forms, vol. 1, pp. 217-223, Marcel Dekker, Inc., New York, New York, (1989).

H.A. Lieberman and L. Lachman (Eds.), Pharmaceutical Dosage Forms, vol. 1, (1970), pp. 132-133, Marcel Dekker Inc., New York NY.

* cited by examiner

*Primary Examiner*—Jake M. Vu

(57) ABSTRACT

A method for providing partial doses of a drug or drugs is disclosed. The method includes breaking of a tablet configured to have an active layer as a first segment and an inactive support layer or substrate as a second segment, or breaking a layered tablet through a first active segment which is deeply or completely scored.

7 Claims, 9 Drawing Sheets

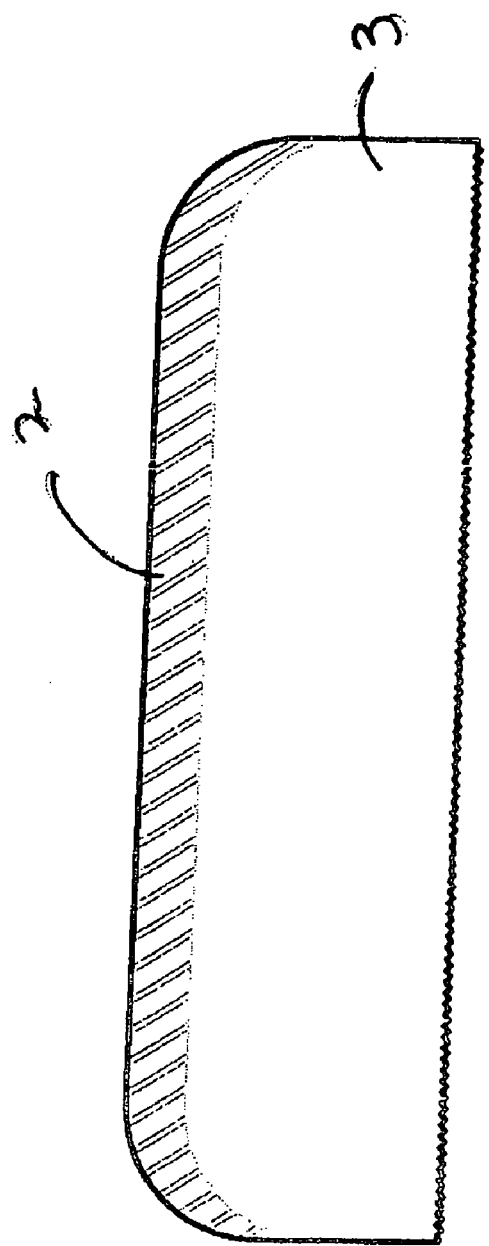
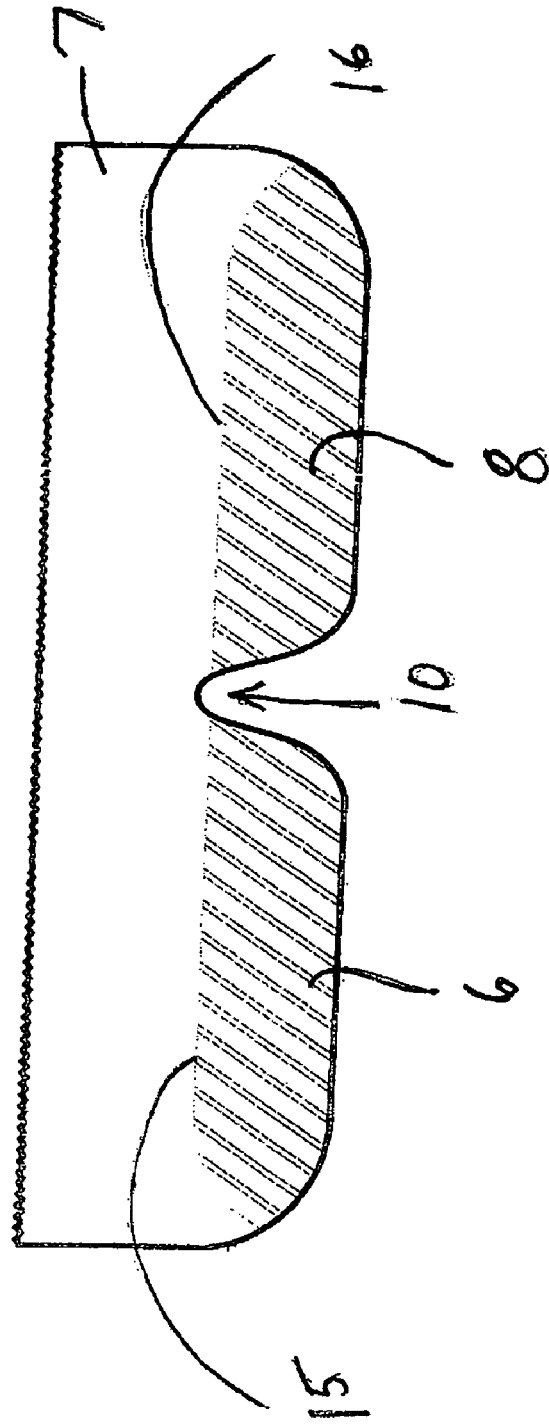
Fig. 8a
Fig. 8b

METHOD OF ADMINISTERING A PARTIAL DOSE USING A SEGMENTED PHARMACEUTICAL TABLET

CROSS-REFERENCE TO RELATED APPLICATIONS

This is a continuation-in-part of International Applications PCT/US2005/018631 and PCT/US2005/018632, filed 23 May 2005, each of which designates the United States and claims the benefit of U.S. Provisional Application Ser. Nos. 60/573,042 and 60/573,134, both filed May 21, 2004.

FIELD OF THE INVENTION

The subject invention concerns a method of administering a partial dose of a compressed pharmaceutical tablet that comprises more than one segment and, in a preferred embodiment, comprises a unitary segment which can optionally be deeply scored.

BACKGROUND OF THE INVENTION

The subject invention derives from the need to solve problems within the pharmaceutical industry relating to inaccurate or inconsistent dose division upon breaking of a dosage form. It is known that pharmaceutical tablets are commonly broken to modify the dose provided in a whole tablet. In the U.S., many "managed care" insurance organizations recommend or encourage patients to split or divide tablets, including unscored or irregularly-shaped tablets. These dosage adjustments, achieved through tablet breaking by patients, have been determined to be imprecise. Various solutions to these problems have been proposed but are of limited use, not being generally applicable to a wide variety of formulations.

Tablets are often produced with a score to aid breaking, but such tablet breaking is well-documented to suffer many problems whether or not scoring of the tablet is provided. Scored pharmaceutical tablets, layered or non-layered, fail to adequately address the problem because of uneven breaking, chipping, or crumbling that occurs upon breaking. Scores formed into a tablet have heretofore not exceeded 1 mm in depth.

In 1984, Stimpel, et al., found that tablet breaking was not accurate, even if performed by a sophisticated, dexterous person. M. Stimpel, et al., "Breaking Tablets in Half." The Lancet (1984):1299.

In a report by Peek et al., "elderly patients" aged 50-79 using, without specific instruction, mechanical tablet splitters to break scored tablets produced highly unsatisfactory division of the tablets. Peek, B.T., Al-Achi, A., Coombs, S.J. "Accuracy of Tablet Splitting by Elderly Patients." The Journal of the American Medical Association 288 No.4 (2002): 139-145. Many drugs, such as warfarin, require dosage adjustments. Peek, et al. found warfarin 5 mg was, on average, split into 1.9 and 3.1 mg tablets when a mechanical tablet splitter was used. This potent anticoagulant has such a narrow therapeutic range that 2.0, 2.5, and 3 mg tablet doses are manufactured. Biron, et al., demonstrated that warfarin 10 mg also often split to less than 4.25 or greater than 5.75 mg. Biron, C., Liczner, P., Hansel, S., Schved, J. F., "Oral Anticoagulant Drugs: Do Not Cut Tablets in Quarters." Thromb Haemost 1201 (1999). In addition, a statistically significant loss of mass resulted from crumbling or chipping when breaking the warfarin tablets.

Rodenhuis, et al., observed that, in 1998, European regulatory authorities started a policy to discourage scoring of tablets. N. Rodenhuis et al., "The rationale of scored tablets as dosage form." European J. of Pharmaceutical Sciences 21 (2004):305-308. Rodenhuis, et al., attributed the new policy to reports of "bad functioning score lines," "tablets difficult to break," and "unsatisfactory mass uniformity of the subdivided halves." Rodenhuis, et al. noted that "[i]mproving the functioning of score lines may be a more practical approach than banning this [scored] dosage form".

US Application 2005/0019407A1 describes composite dosage forms having first and second portions joined at an interface. These dosage forms have a first molded material and a second compressed material. No disclosure is provided to teach or suggest any modification to facilitate the breaking or subdividing the dosage forms or providing a partial dose.

The present invention, as disclosed herein, can overcome or alleviate the problems discussed above, and can provide additional advantages and address other problems as would be well understood and recognized from this disclosure by persons of ordinary skill in this art.

SUMMARY OF THE INVENTION

The present invention is directed to a method of providing to a patient a partial dose of a drug or drugs contained in a layered tablet. A "patient", as used herein, refers to any animal in need of the administered drug and can be, but is not limited to, a mammal, preferably a human.

A novel tablet configuration consisting essentially of two layers, where a first layer comprises a pharmacologically effective amount of a drug or drugs (hereinafter, an "active layer") and a second layer which comprises a pharmaceutically acceptable composition substantially free of a pharmacologically effective amount of drug or drugs (hereinafter, "inactive layer") can advantageously provide structural integrity to the layered tablet.

This configuration can also advantageously minimize loss of mass of active drug during tablet breaking to make a tablette (defined herein) and administering the tablette to provide a partial dose of a drug or drugs. Therefore, a method of the subject invention includes the breaking of this novel dosage form having a first active layer containing a whole dose, and a second inactive layer, to produce a tablette comprising a partial dose, then administering to a patient the partial dose in the tablette.

More specifically, a preferred method thus comprises the steps of:
 a) providing a tablet consisting essentially of a first segment containing a drug or drugs and a second inactive or substantially drug-free segment;
 b) breaking the tablet to create a tablette comprising the partial dose; and
 c) administering the tablette to a patient in need of treatment employing the partial dose of the drug or drugs.

The segments can be scored or unscored. In a preferred embodiment, the dosage form comprises a first segment which is scored and a second segment which is unscored. More preferably, the first segment is deeply scored, or scored 50% or more through its height. If unscored, or if the score does not completely transect the active segment, then step b), above, will necessarily include breaking through the first segment and second segment.

In an embodiment of the invention utilizing a deeply scored segmented tablet, the method comprises the steps of:
 a) providing a compressed pharmaceutical tablet comprising a first segment and a second segment, the first segment containing active ingredient and having a score at least 50% through the first segment;

b) breaking through at least said second segment of the tablet at the score in said first segment to create a tablette, and c) administering the tablette to a patient in need of treatment employing the partial dose of the drug or drugs.

The method of the invention utilizes a pharmaceutical tablet having two or more segments, wherein a first segment includes a pharmacologically effective amount of a drug or drugs and has a score that extends into said first segment at least 50% of the distance from a surface of said first segment towards an opposite face (surface) of said first segment having on said opposite face, an adjoining second segment. In one preferred embodiment, the score does not extend completely through the first segment, and may extend up to, but not into, the second segment and preferably extends from about 70% to about 99.5% of the "height" distance of the first segment.

In another preferred embodiment, the score may be formed completely through the height of the first layer, continuing into, or being in "contact" with, the second segment. This complete division of the first layer (as viewed in cross section) therefore forms two separate segments from that first layer. Thus, a tablet configuration formed from substantially two layers can provide three segments: two segments from the first layer and a third segment from the second layer. See, for example, FIG. 4 and its accompanying description. These divided segments are, technically, unscored in final form because they are divided into two separate, unscored segments. However, because these divided segments may be formed by scoring 100% or greater through a first segment, a tablet comprising these divided segments may be included as a "scored" or "deeply scored" tablet for purposes of understanding this invention. Notably, a score formed greater than 100% through a first segment forms a score into the second segment. Therefore, the two-layered tablet scored more than 100% through the first segment is, technically, a "scored" three-segment tablet.

Also preferably, the second segment has a lesser amount of drug than the first segment (or segments in a tablet having a completely scored, or divided, first segment), ranging from no drug, or an undetectable amount of drug, up to about 80% of the concentration of the drug in said first segment.

The concentration of a drug or drugs in a segment means the ratio, on a weight to weight basis, of the drug or drugs in said segment to the total weight of said segment. The total weight of the segment includes drug or drugs and inactive excipients.

A preferred method of the invention utilizes a two-segment tablet, formed from a first composition, e.g., a granulation, comprising active drug, preferably in a therapeutically effective quantity and a second segment formed from a composition, e.g., a granulation, comprising inactive excipients. In this embodiment, a deep score can be provided that preferably extends substantially, but not completely, through said first segment, so that breaking said tablet through said score creates two new portions of the tablet each having a substantially predetermined quantity of active drug therein.

Tablet portions comprising a partial dose are denoted herein as "tablettes". A tablette is formed when a whole tablet is broken into one or more tablet portions such that an intended partial dose of active drug remains in each tablet portion. A tablette resulting from the breaking of a tablet can be further broken into additional portions, which are also "tablettes". Typically, tablets utilized in the method of the invention are intended to be broken in half through a score by an end user. Tablet breaking creates two major tablet fragments, each of which is a tablette. Crumbs and small chips that are formed incidental to the breaking process are not considered to be tablettes.

Another preferred method involves utilizing the above-described tablet structure as a core part of a larger tablet, so that administration can be made of a partial dose from a tablet containing three segments, each derived from the following formulations: a first segment containing drug and being deeply scored, a second (middle) segment derived from an inactive composition, and a third segment derived from a formulation containing drug that is optionally scored. In said tablet, the layers are arranged ("disposed") vertically one on top of another, and the first or third segment (or both) contains a deep score that most preferably extends more than 90% through said segment, nearly reaching the second, or middle, segment. The active ingredients comprising said first and third segments may be identical or different and are not limited.

Other embodiments are discussed herein or would be apparent to a person of ordinary skill in the art based on the provided disclosure and from the accompanying drawings.

BRIEF DESCRIPTION OF THE DRAWINGS

FIGS. 8a and 8b depict two tablettes made by breaking the tablet of FIG. 7.

DETAILED DESCRIPTION OF THE INVENTION

Figure 1:
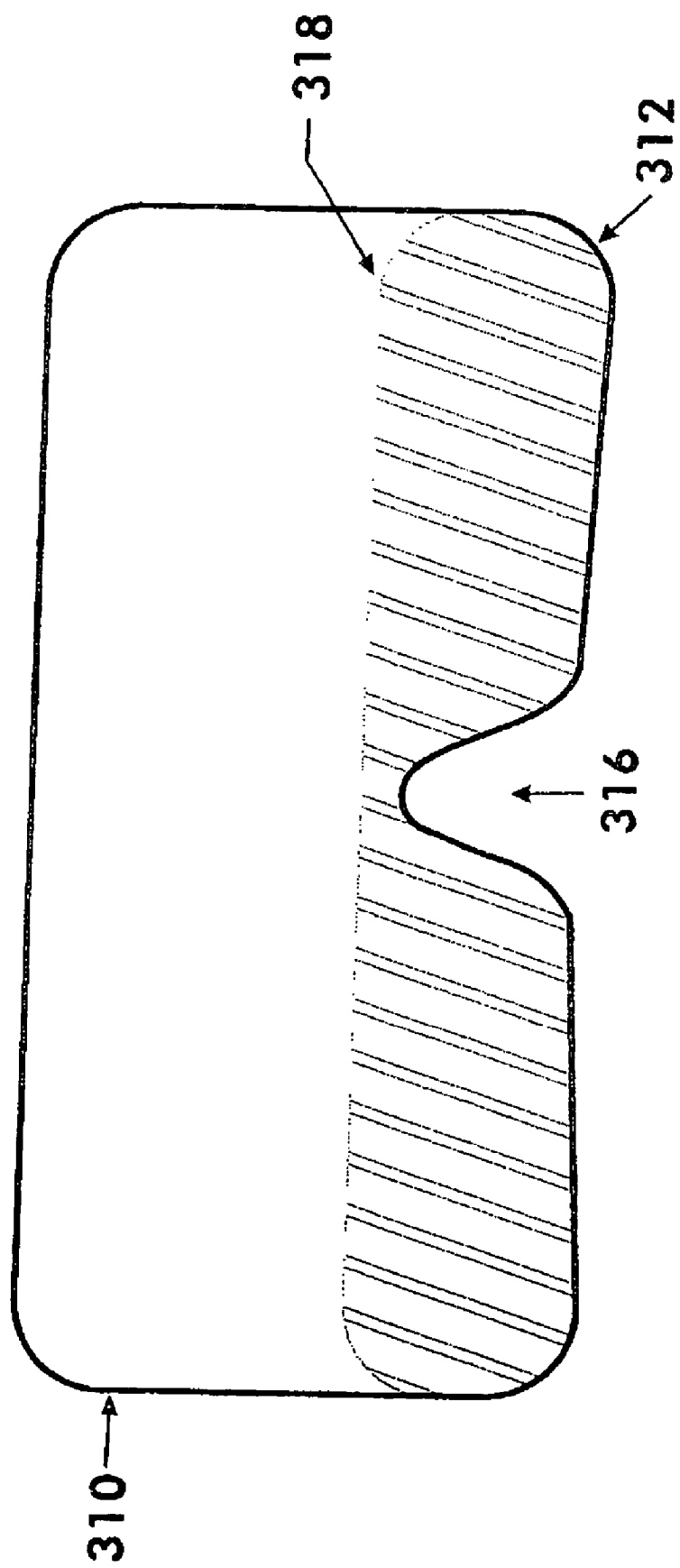
FIG. 1 depicts a cross section of a tablet adapted for use in the invention which has two segments and one score.

The subject invention is directed to a method of administering a partial dose of a drug or drugs derived from a pharmaceutical tablet, preferably a pharmaceutical tablet which is made by compression such as by compression applied in a die in an automated tabletting machine. It is to be understood that in describing and claiming the present invention, the following terminology will be used in accordance with the definitions set out below for the purpose of providing a general understanding and is not intended to be limiting.

A "segment" represents the entirety of a substantially homogeneous contiguous region of a tablet or tablette (see below) of the invention. Segments are formed from layers, which are formed from compositions such as granulations. If two substantially identical granulations enter the die sequentially, one on top of the other, thus forming two layers, and are compressed together, a compound segment, i.e., one formed from more than one substantially identical layer would be formed. If, however, two granulations containing different active drugs are compressed one onto the other, the two granulations form two segments. Granulations comprising the same active drug but with dissimilar excipients would also comprise two segments if one granulation were compressed onto another.

A compressed layer that is not adjacent to a layer formed from a substantially identical granulation that formed said first-mentioned layer is denoted a "simple segment." Tablets of the invention comprise, without limitation, two or more segments, and each segment may be formed from two or more layers, though more typically in the invention a segment or segments will be formed from one layer and not a plurality of layers.

A "layer" is a tablet structure that is made by introducing an amount of an individual granulation into a tablet die to fill at least a part of the die. A layer is considered to be present whether it is in the form of an un-tamped, tamped or fully compressed granulation. Because some powder migration of material may take place between granulations and layers in the tabletting machine, some amounts of granulations forming a layer may be transferred to another layer or all other layers; in the most preferred embodiments of the invention, such an effect is not pharmacologically significant.

The terms "active agent," "active drug," "drug," "active pharmaceutical ingredient" and "pharmacologically active agent" are interchangeable herein and refer to a chemical material or compound which, when administered to an organism (human or animal) induces a pharmacological effect, and which includes prescription and non-prescription pharmaceutical compounds, as well as pharmacologically effective doses of vitamins, co-factors and the like. Not considered to be drugs herein are such substances as foodstuffs and vitamins in "recommended daily allowance" quantities.

The term "interface" refers to that part of the tablet representing the region at which two segments adjoin one another.

The term "undetectable amount" means that when using conventional analytical techniques such as high performance liquid chromatography (HPLC), nuclear magnetic resonance imaging (NMRI) and the like, the presence of an active compound cannot be detected. The term "pharmacologically ineffective amount" means that any amount of drug detected has no detectable pharmacological effect. It is understood that due to the conditions under which high speed automated tabletting equipment are operated, some unintentional mixing of different granulations may occur which may cause some amounts of one granulation to appear in a segment where it was not intended to be placed. The terms "horizontal," "transverse," and "vertical" when used in relation to a tablet, are based on the spatial orientation of the tablet as, and after, it is produced in a die, but before removal or ejection from the die.

Tablets adapted for use in the invention are most conveniently manufactured, for commercial or research use, on a high-speed tablet press that has a plurality of filling stations. A tablet press provided with exactly two filling stations is typically referred to as a bilayer press; a tablet press provided with exactly three filling stations is typically referred to as a tri-layer press, etc. A "five-layer" press is commercially available (Korsch AG, Germany). Some tablets of the invention may be manufactured on a bilayer press, and others require a tri-layer or a five-layer press.

Tablets adapted for use in the invention may be manufactured using one granulation comprising a drug or mixture of drugs and a second granulation containing optionally an undetectable amount of drug or a pharmacologically ineffective amount of drug, or containing the same drug or drugs, or a different drug or drugs. The basic, most preferred tablet of the invention may be produced with different techniques.

Tablets useful in the subject invention are described in International Patent Applications PCT/US2005/018631 and PCT/US2005/018632, and their progeny, which are incorporated herein by reference.

For example, FIG. 1 demonstrates a bilayer tablet adapted for use in the present invention. Production may involve first allowing a granulation containing active drug into a die that has an embossed lower punch, so that said granulation forms an undivided layer indented from below by said embossing. Said embossing is not limited in its pattern. After optional and preferred tamping, an inactive granulation enters the die and after optional pre-compression, a tablet is formed by final, full-force compression. This compression pushes the first, lower layer almost to the level of the uppermost aspect of the embossing, so that an especially deep score may be produced. Each granulation, after entry into the die, forms a layer. After final compression of the tablet, each layer may also be referred to as a segment of the tablet. Except for inadvertent mixing between granulations, the upper segment is inactive, so that tablet breaking may occur substantially through the inactive segment, thus providing substantial improvement over existing methods of scoring tablets from the standpoint of accuracy of subdividing a dose. Less preferably, the second granulation could contain a diluted quantity of the active ingredient or ingredients comprising said first granulation. Such a maneuver would be useful if it were difficult to place adequate drug substance entirely within said first granulation.

In the case in which it is desired to provide additional active drug in a segment above the deeply scored segment, a trilayer design could be useful, given certain practical limitations regarding the height of embossings. In this example, a highly concentrated granulation of drug forms the first granulation, which is pushed as close to the top of the embossing as possible; a second, less concentrated (w/w %) granulation comprising the identical active ingredient enters the die, and a third, inactive granulation finally enters the die. After final compression, a tablet that is preferably very deeply scored with respect to the first segment will have been created, and the middle segment, which will tend to break more accurately than the outer segment, improves the accuracy of said tablet breaking relative to a tablet of simpler design.

A different mode of manufacture may be employed, using an embossed upper punch and a preferably flat-faced lower punch. In this technique, a most preferred tablet adapted for use in the invention may be produced as follows. A first, inactive granulation enters the die and is optionally tamped. A second granulation comprising drug then enters the die, is optionally tamped, and final compression occurs. Some amount of drug lies under the lower part of said embossing but the bulk of second granulation is apart from the breaking area, and thus when and if force is applied in a conventional, vertical fashion to the lowest aspect of the score, highly accurate tablet breaking will take place with respect to the active drug.

As used herein, such terms as "horizontal" ("transverse") and "vertical" when used in relation to a tablet, are based on the spatial orientation of the tablet as, and after, it is produced in a die, but before removal or ejection from the die. Current methods of manufacture produce tablets with one granulation entering the die on top of another, so that tablets of the invention produced in such a manner comprise one or more top (outer) segments, one or more bottom (outer) segments, and optionally one or more middle (inner) segments. A segment that is not a top or bottom (i.e., outer) segment is considered to be an inner segment.

If a tabletting machine were developed that allowed tablet manufacture to occur so that separate granulations could be sequentially placed in a die horizontally (side-to-side) and not vertically as is currently the practice, then the tablets so produced would be within the scope of the present invention as the same product would be produced.

Tablets adapted for use in the invention are not limited as to the dimension of the tablet, nature or number of active ingredients, type of excipients, or depth of the score. The depth or height of the score reflect the dimensions of said embossings. Conventional embossings are less than one (1) mm in vertical dimension from the adjacent base of the punch on which the embossings are placed. In practice, three (3) mm may be a practical upper limit for the height of an embossing.

Another technique to provide a score is to cut into a tablet, such as with a knife or a high-speed cutting apparatus, at a desired location on the tablet subsequent to tablet compression or other means of tablet formation. The tablets of the invention are best broken transversely in order to realize their benefits. Tablets may be broken in standard ways such as either by applying force such as a cutting edge directly to the desired breaking region, or to other areas of the tablet to realize the same effect.

The figuers depict tablets and tablettes adapted for use in the method of the subject invention. Front views of the tablets are depicted as they are positioned in the die, so that the top of the tablet as shown on the page corresponds with the top of the tablet in the die. In other words, the top segment of the tablet as shown contains the last granulation to enter the die.

"Front views" refer to a cross-sectional view of a tablet that has a theoretical geometric plane passed through the tablet relative to a side which is arbitrarily designated as the front. Figures labeled as "side view," which also have a corresponding "front view," are taken as a cross-section through the whole tablet from the right side of a front view, i.e., a side view is a cross-section that is taken by passing a plane through the vertical axis of the whole tablet at a 90° angle to the cross-sectional front view. Each front view represents a schematic cross-section that passes through the midpoint of the horizontal cross-section as measured from the front of the tablet to the back of the tablet or tablette. The front view is also parallel to the major axis of the tablet (e.g., for a tablet with a rectangular (but not square) transverse cross-section, the longer side of the perimeter is parallel with the plane that depicts the cross-sectional, front view). That plane is located half-way between the front and back surfaces of said tablet.

Tablettes are also depicted as they would exist in relation to the tablet die in which they are formed. For consistency, tablettes are depicted in the same orientation as the tablets from which they are formed, although tablettes are created after tablet formation and ejection from the die. Tablettes are depicted with broken surfaces as indicated by a fine saw-tooth pattern. Such saw-tooth depiction is schematic and not intended to represent the actual pattern of breaking of a tablet.

FIG. 1 depicts a tablet with a score 316 that extends approximately 90% through the bottom segment 312 which contains active drug. Upper segment 310 allows structural stability of the tablet despite the deep score 316 and can be an inactive segment (containing no active drug) or can include a different concentration or different drug from the active contained in bottom segment 312. Interface 318 is present.

Figures 2A, 2B:
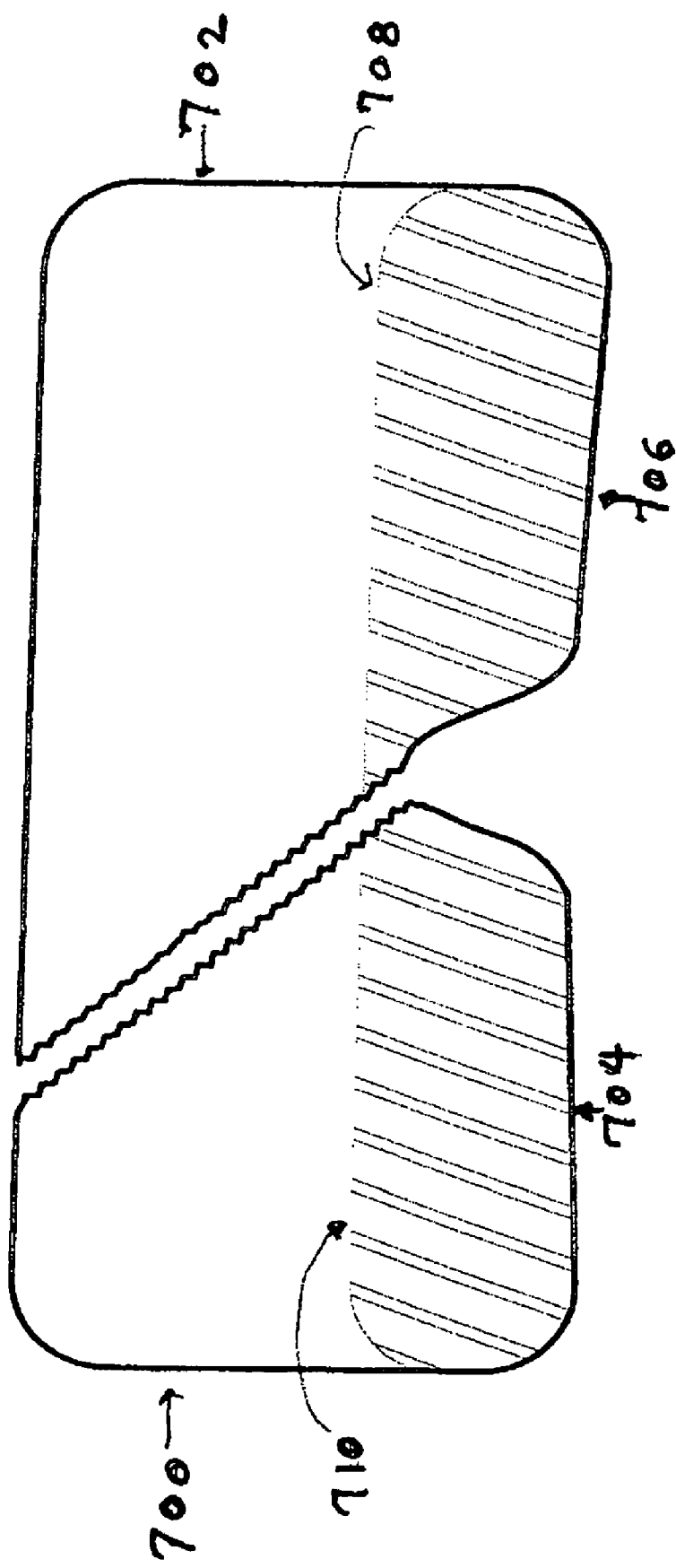
FIG. 2 depicts a cross section of a tablet of FIG. 1 broken into two tablettes for use in the invention, each tablette having two segments.

Breaking the tablet of FIG. 1 in accordance with the method of the subject invention gives two tablettes as shown in FIG. 2. Segment 310 of FIG. 1 has been divided into two segments, 700 in the smaller tablette and 702 in the larger tablette. Even though the break, as illustrated, is far from vertical, it is clear that the amount of drug is similar in each of the newly formed tablette segments 314 and 315. Two new active segments, 706 and 704, are created by breaking the whole tablet into the two tablettes. New interfaces 708 and 710 lie at the regions at which segments 702 and 706, and 700 and 704, respectively, adjoin.

Figure 3:
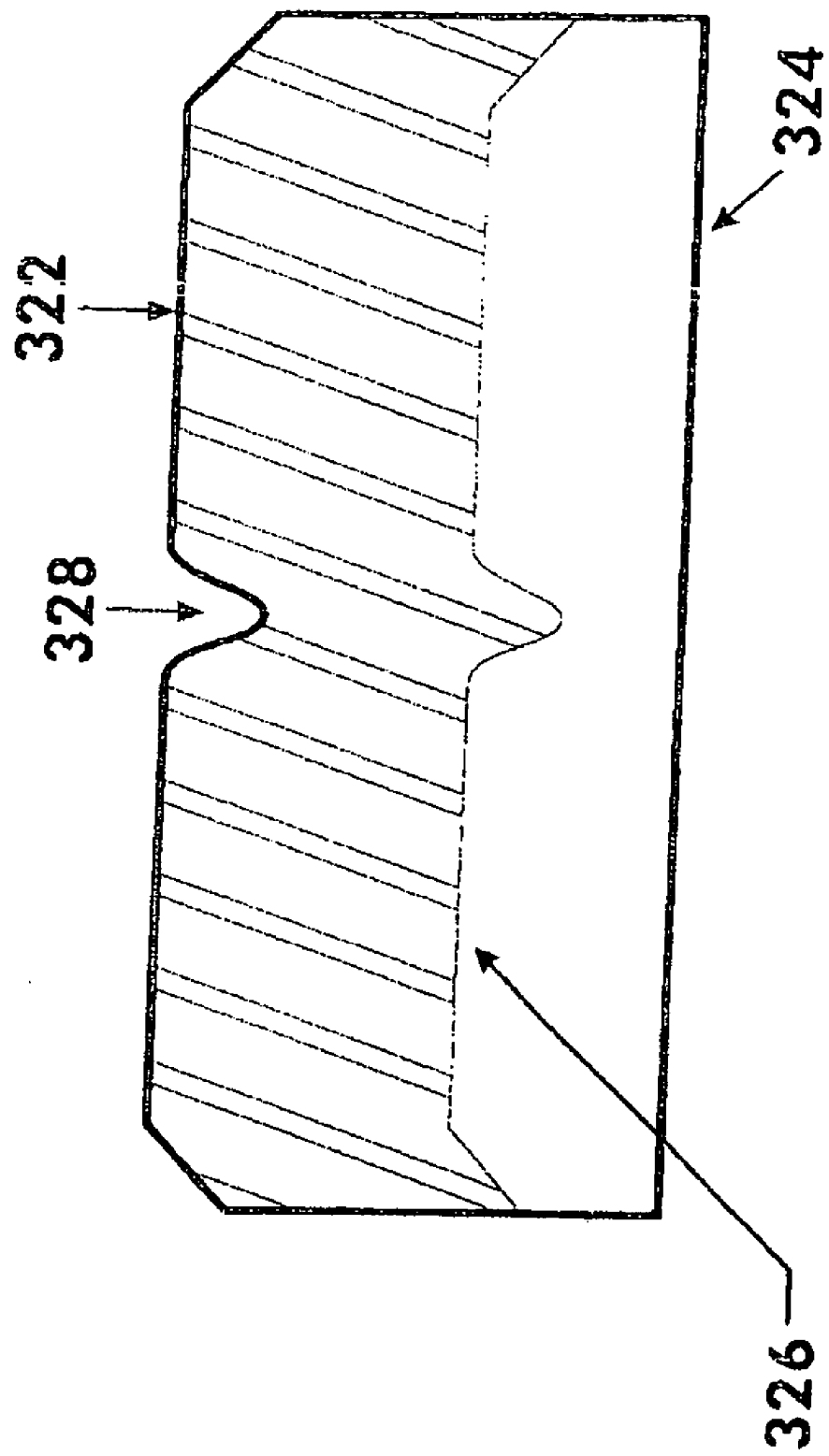
FIG. 3 depicts a cross section of a tablet adapted for use in the invention with two segments and one score.

FIG. 3 demonstrates a pharmaceutical tablet adapted for use in the method of the subject invention with an upper segment 322 with a score 328 that is not deep. The tablet bottom segment 324 lacks a pharmacologically effective dose of a drug. Interface 326 depicts the region at which the segments adjoin.

Figure 4:
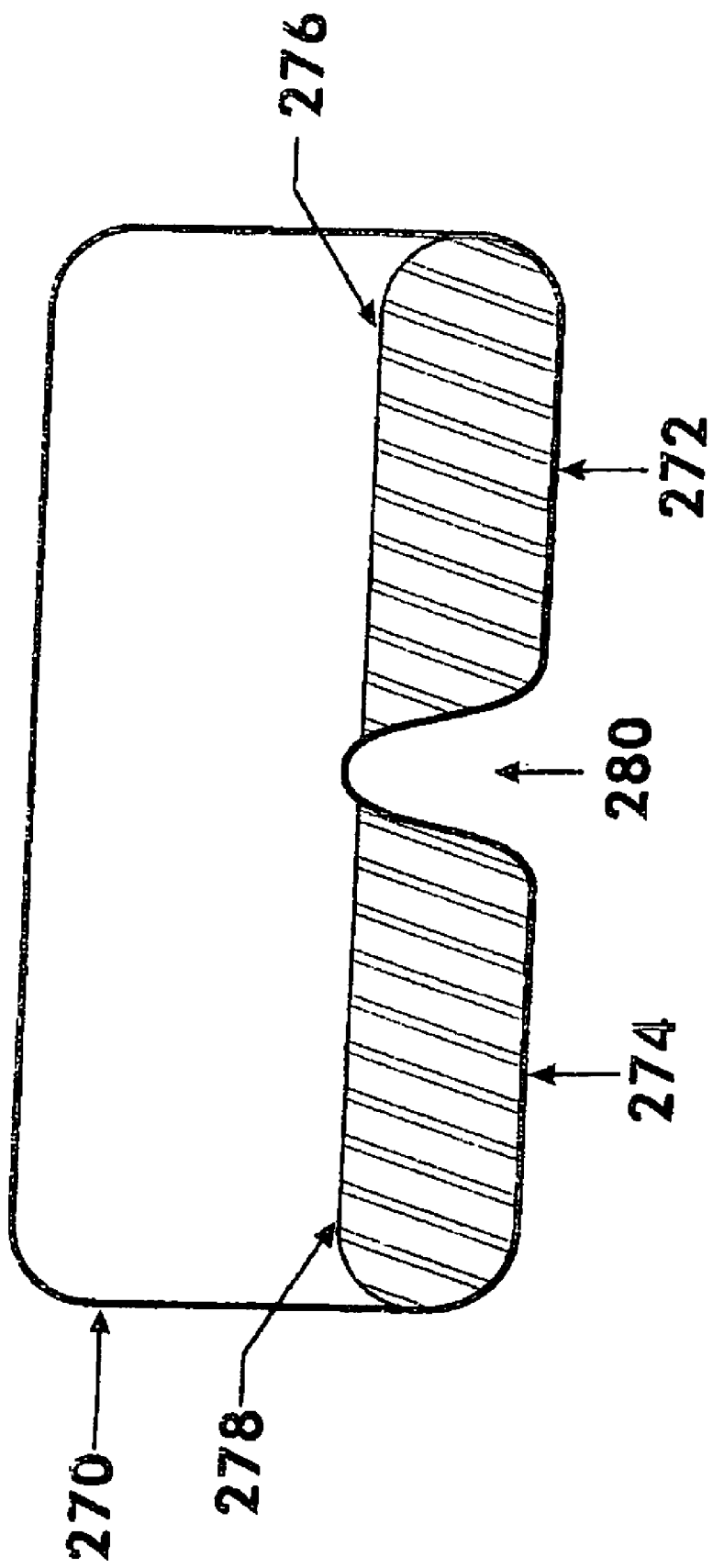
FIG. 4 depicts a cross-section of a three-segment tablet with one score. In cross section, the complete separation of the first layer provides two segments within that first layer; the third segment is provided by the second layer.

FIG. 4 depicts a tablet containing unitary segments 272 and 274 in vertical cross-section, front view. Both of said unitary segments adjoin the same face (surface) of. segment 270, which is formed from a single granulation and due to mixing of granulations, contains a minimal amount of the drug that is present in segments 272 and 274. Interfaces 276 and 278 represent the regions at which segment 270 adjoins segments 272 and 274, respectively. Score 280 indents segment 270 and also represents the space between segments 272 and 274.

Figures 5A, 5B:
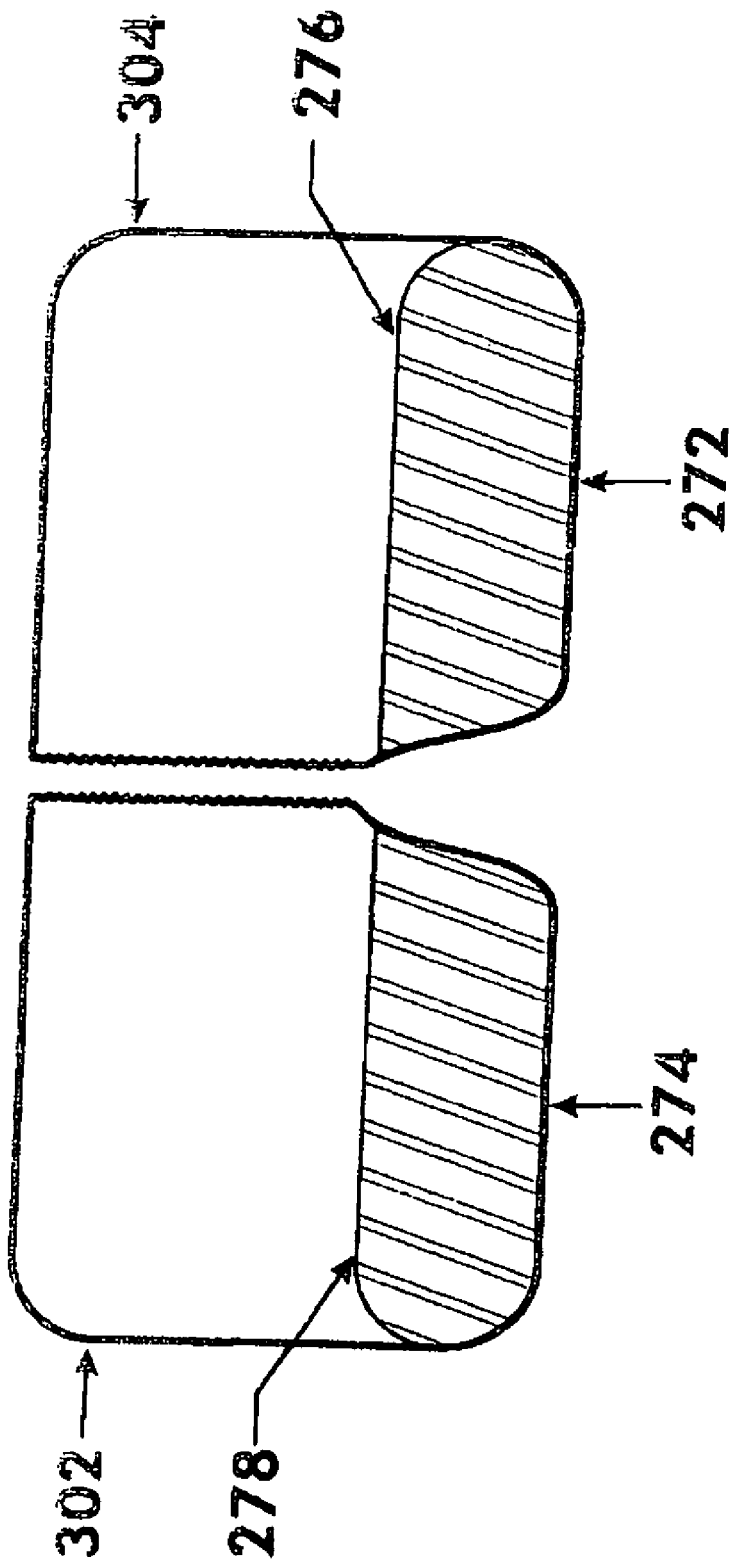
FIGS. 5a and 5b depict cross-sections of the tablettes made by breaking the tablet of FIG. 4 at the score.

FIGS. 5a and 5b depict the two tablettes created by breaking the tablet of FIG. 4 through segment 270. In FIG. 5a, segment 302 represents that part of segment 270 that adjoins intact segment 274. Interface 278 represents the region at which segments 302 and 274 meet. In FIG. 5b, interface 276 represents the region at which segments 304 and 272 meet. Score 280 and segment 270 of FIG. 4 are not considered to exist once the tablettes are formed. Each tablette of FIGS. 5a and 5b contains substantially equivalent mass assuming the score 280 of FIG. 4 is a bisecting score relative to the layer that became divided in the creation of segments 272 and 274.

Tablets of the nature of that of FIG. 4 may contain in the unitary segments a mixture of drugs or, as in FIG. 4, one drug. In addition, the granulation that forms segment 270 of FIG. 4 may be provided with a drug that is the same as, or different than, that of the divided layer. In this case, it would be likely that said drug provided in the upper layer would have a therapeutic effect and side effect profile that was not very sensitive to accuracy of subdivision of a dose.

In addition, no limitation exists as to the presence of one or more additional segments created superior to (i.e., above) 270, or the composition of such. Also, though less likely, there could be another set of different unitary segments inferior to (i.e., below) segments 272 and 274.

Figure 6A:
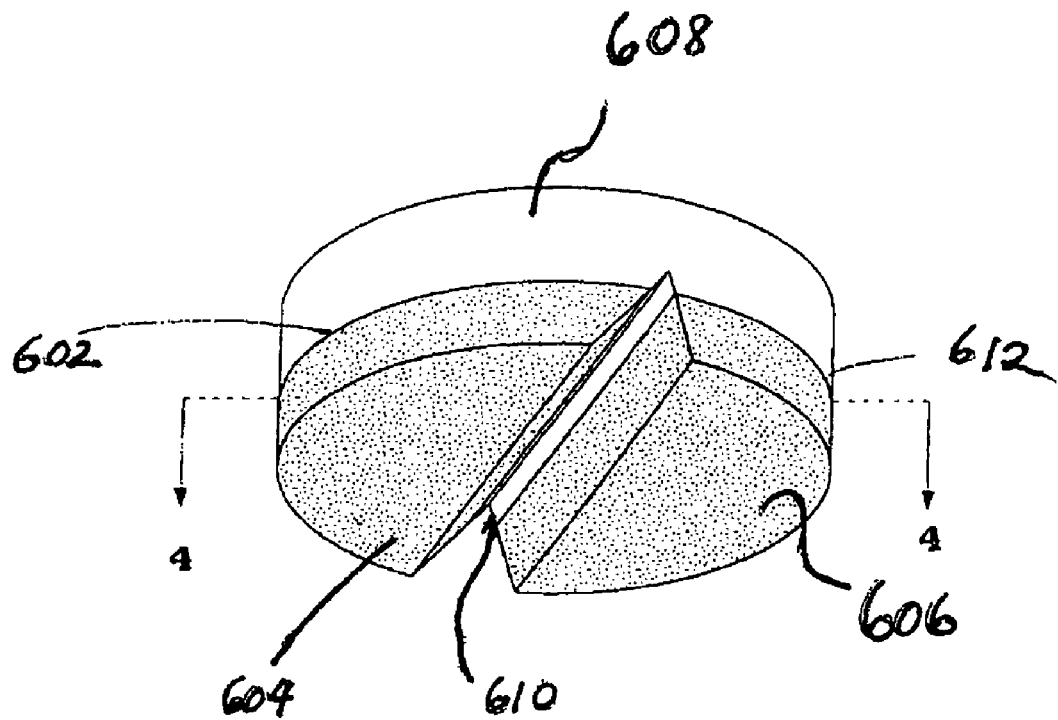
FIG. 6a depicts a bottom perspective view of a three segment tablet.

FIG. 6a depicts an external view of a tablet containing unitary segments 604 and 606 that are at the bottom of the tablet. In this tablet, score 610 penetrates into clear, upper, non-unitary segment 608. Interface 602 represents the region at which segment 608 meets segment 604. Interface 612 represents the region at which segment 606 meets segment 608.

Figure 6B:
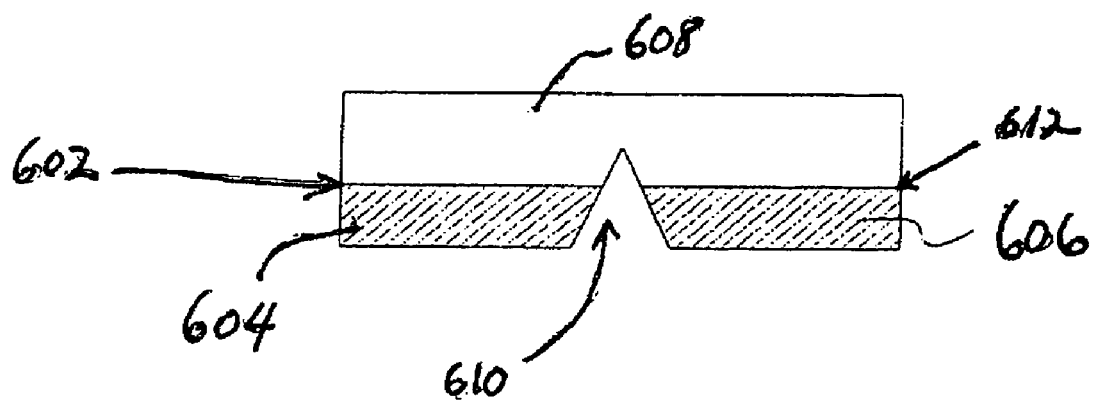
FIG. 6b is a cross-section of FIG. 6a taken along lines 4-4.

FIG. 6b depicts the same tablet depicted in FIG. 6a. This vertical cross-section is taken perpendicularly through score 610, which occupies the diameter of the circular transverse cross-section of the tablet.

Figure 7:
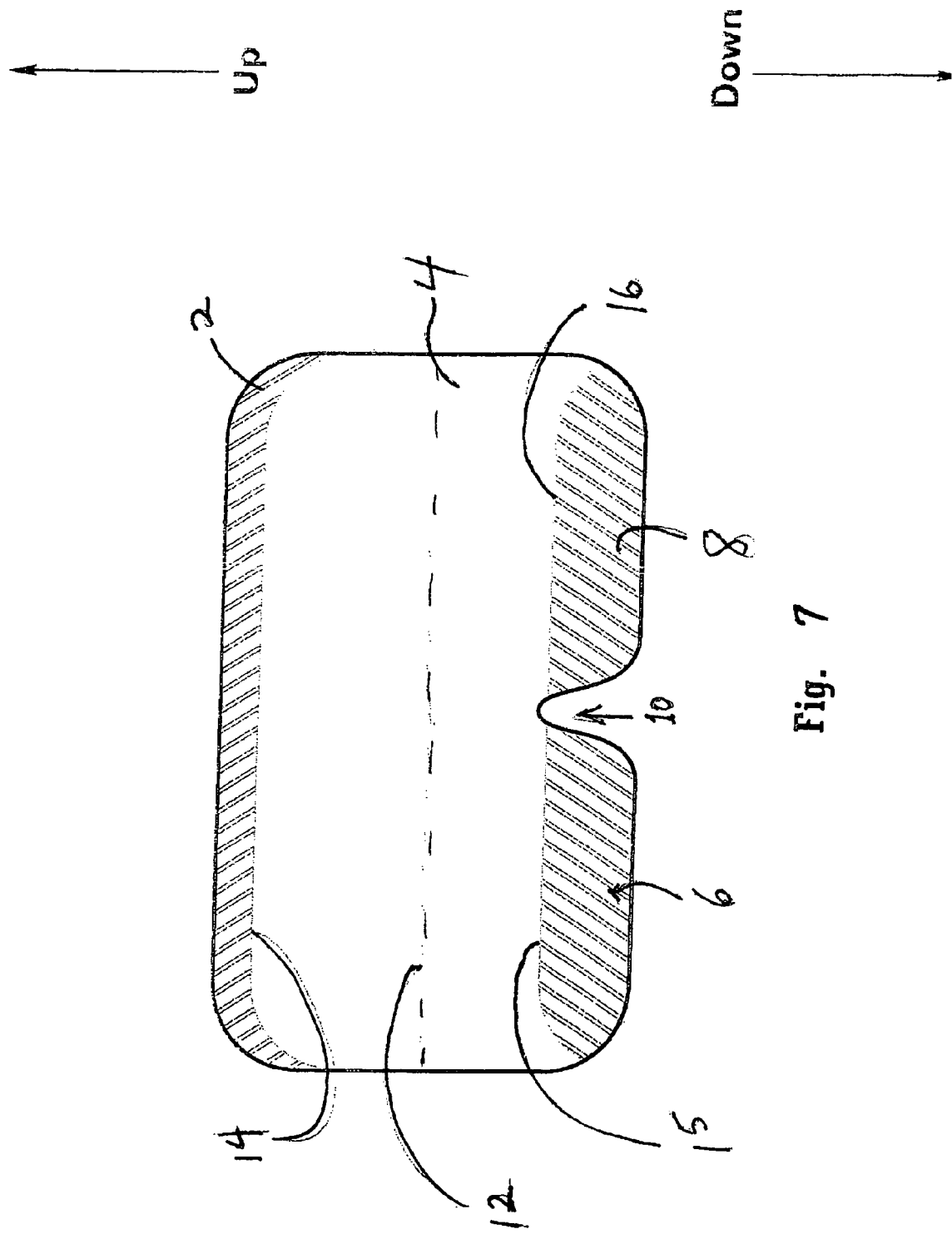
FIG. 7 is a cross-section of a scored four segment tablet.

FIG. 7 depicts a tablet containing four segments. Unitary segments 6 and 8, as with all unitary segments, are not contiguous with each other. Score 10 penetrates into segment 4. Segment 4 is a compound segment formed from substantially compositionally identical inactive granulations added sequentially. Top segment 2 contains a therapeutic quantity of a drug that differs from the drug that is present in a therapeutic quantity in segments 6 and 8. Dotted line 12 reflects a surface score that runs transversely across segment 4. A preferred horizontal dimension for the tablet of FIG. 7 is 12-18 mm, but said dimension is not limited. Interface 14 depicts where segments 2 and 4 are contiguous. Interfaces 15 and 16 depict where segments 6 and 8, respectively, adjoin segment 4. Segment 4 contains therapeutically insignificant quantities of the drugs found in segments 6 and 2.

The tablet of FIG. 7 may be broken usefully in two ways. One way is vertically through score 10 in the direction of segment 2; such breaking would not utilize the score reflected by dotted line 12, but would give a dose of about half of the drug found in segments 6 and 8, though likely would not give precise halving of the drug in segment 2. The result of another way of breaking said tablet is depicted in FIGS. 8*a* and 8*b*.

FIG. 8*a* shows a tablette formed from breaking the tablet of FIG. 7 through the horizontal score reflected by dotted line 12. As with other tablettes depicted herein, it is not assumed that breaking is even, but the tablettes are depicted so that breaking is contained substantially within segment 12, that is a segment interposed between upper segment 2 and lower segments 6 and 8 in the tablet of FIG. 5. The tablette of FIG. 8*a* demonstrates that segment 2 is intact, as is interface 14. Segment 3 is formed by the part of therapeutically inactive segment 4 of the tablet of FIG. 7 that remains contiguous with segment 2. The tablette of FIG. 8*b* depicts segments 6 and 8, and interfaces 15 and 16, as unchanged from the tablet of FIG. 7. Segment 7 is the part of segment 4 of FIG. 7 that becomes part of the tablette of FIG. 8*b*.

Figure 9B:
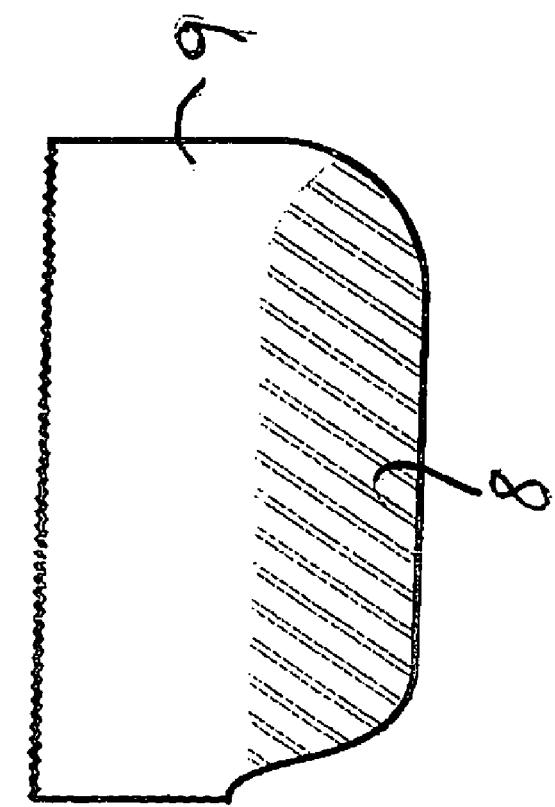
FIGS. 9a and 9b depict two tablettes made by breaking one of the tablettes of FIG. 8b.
Figure 9A:
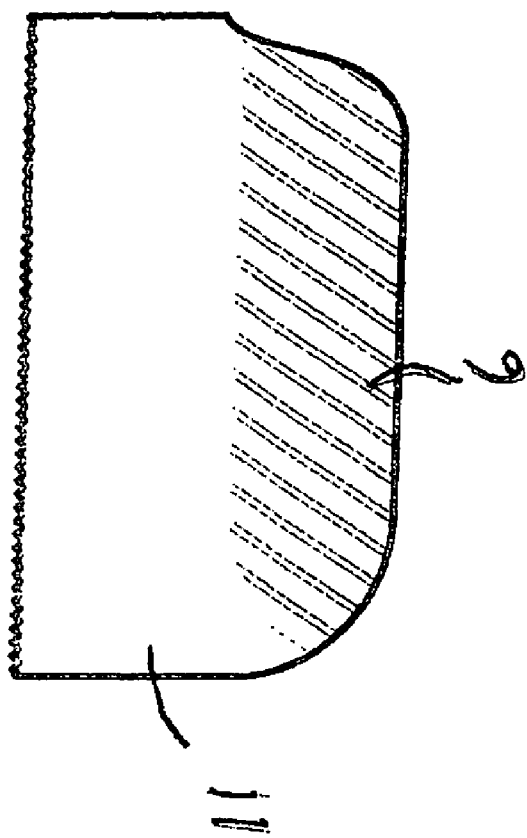

FIGS. 9*a* and 9*b* depict the result of a second breaking, that of the tablette of FIG. 8*b*. FIG. 9*a* depicts segment 8 that now adjoins new segment 11, formed from segment 7 of the tablette of FIG. 8*b*. Interface 16 and segment 8 are unchanged from that of the whole tablet of FIG. 7.

FIG. 9*b* depicts segment 9, formed from segment 7 of FIG. 8*b*, and segment 6 and interface 15, which are unchanged from the whole tablet of FIG. 7.

Thus, FIGS. 7*a* and 7*b*, in association with FIGS. 5, 6*a*, and 6*b*, demonstrate a means by which a combination tablet can be divided not only to separate therapeutic quantities of one active drug from another, but also then precisely give a partial dose of one of said active drugs.

The invention enables administration of a part of a tablet because accurate dosing is provided when a tablet (or tablette) of the invention is broken as described herein. In addition, the ability to separate one active drug from another in a combination product has cost saving advantages as well.

It is recognized that related inventions may be within the spirit of the disclosures herein. Also no omission in the current application is intended to limit the inventors to the current claims or disclosures. While certain preferred and alternative embodiments of the invention have been set forth for purposes of disclosing the invention, modifications to the disclosed embodiments may occur to those who are skilled in the art.

The invention claimed is:

1. A method of providing a partial dose of a drug or drugs contained in a layered tablet, said method comprising:
   a) providing a bi-layer tablet comprising two or more segments wherein a first layer is scored, forming one or more segments comprising a composition containing a drug or drugs, and a second layer forming a segment comprising an inactive or drug-free composition, said second inactive layer or segment providing structural integrity to, and accurate tablet breaking for, the scored tablet;
   b) dividing said tablet through said first and second segments to create a tablette comprising the partial dose; and
   c) administering to a patient in need of treatment said tablette containing the partial dose of the drug or drugs.

2. The method of claim 1 in which the score is at least about 70% through said first segment.

3. The method of claim 1 wherein said score traverses 100% through said first segment.

4. The method of claim 1 wherein said tablet is an immediate release dosage form.

5. A method of providing a partial dose of a drug or drugs contained in a layered tablet, said method comprising:
   a) providing a bi-layer tablet comprising two or more segments wherein a first layer is scored, forming one or more segments comprising a composition containing a drug or drugs, and a second layer forming a segment comprising an inactive composition or drug-free composition, said second layer or segment providing structural integrity to, and accurate tablet breaking for, the scored tablet;
   b) directing or instructing a user of said tablet to divide said tablet through said first and second segments to create a tablette for administration of said tablette to a patient in need of treatment using said partial dose of the drug or drugs.

6. The method of claim 5 in which the score is at least about 70% through said first segment.

7. The method of claim 5 wherein said tablet is an immediate release dosage form.

* * * * *